United States Patent [19]
Baba et al.

[11] Patent Number: 5,600,701
[45] Date of Patent: Feb. 4, 1997

[54] X-RAY IMAGING SYSTEM AND METHOD THEREFOR

[75] Inventors: Rika Baba, Kokubunji; Ken Ueda, Ome; Yoichi Onodera, Asaka; Keiji Umetani, Hino; Hisatake Yokouchi, Tokyo; Shigekazu Hara, Noda; Tomoharu Kajiyama, Koganei; Fumitaka Takahashi, Toride, all of Japan

[73] Assignee: Hitachi Medical Corporation, Tokyo, Japan

[21] Appl. No.: 240,313

[22] Filed: May 10, 1994

[30] Foreign Application Priority Data

| May 11, 1993 | [JP] | Japan | 5-109141 |
| Aug. 19, 1993 | [JP] | Japan | 5-205164 |

[51] Int. Cl.⁶ .................................................. H05G 1/64
[52] U.S. Cl. ............................................ 378/98.2; 348/634
[58] Field of Search ............................. 378/62, 98, 98.2, 378/98.4, 98.12; 348/634

[56] References Cited

U.S. PATENT DOCUMENTS

| 4,672,559 | 6/1987 | Jansson et al. | 364/525 |
| 4,829,552 | 5/1989 | Rossi et al. | 378/154 |
| 4,868,747 | 9/1989 | Mori et al. | 364/413.18 |
| 5,229,618 | 7/1993 | Nakajima | 250/559 |
| 5,231,673 | 7/1993 | Elenga | 382/6 |
| 5,263,074 | 11/1993 | Sakamoto | 378/99 |
| 5,331,553 | 7/1994 | Muehllehner et al. | 364/413.24 |
| 5,349,625 | 9/1994 | Born et al. | 378/95 |
| 5,375,156 | 12/1994 | Kuo-Petravic et al. | 378/9 |
| 5,396,347 | 3/1995 | Kaneko | 358/448 |
| 5,485,500 | 1/1996 | Baba et al. | 378/98.2 |

FOREIGN PATENT DOCUMENTS

| 60-50900 | 3/1985 | Japan. |
| 210636 | 1/1990 | Japan. |
| 528316 | 4/1993 | Japan. |

OTHER PUBLICATIONS

Rika Baba, et al.; Chest Radiography using Partial Exposures and Image Synthesis; Japanese Journal of Medical Electroncis and Boi. Eng., vol. 31., p. 209.
Fundamentals of Medicine and Pharmacy I; p. 123 (1981).
Th. Hilbertz, et al.; Perivision — a new standard in peripheral angiography; Electromedica 60 (1992) No. 1, pp. 2–5.
Satsuzo Kogaku "(Imaging Pickup Engineering)" Corona Publishing Co., Ltd. (1995) pp. 37–40.

*Primary Examiner*—Don Wong
*Attorney, Agent, or Firm*—Antonelli, Terry, Stout & Kraus

[57] ABSTRACT

In order to image an object larger than a field of view for observation, imaging is effected by dividing it into several times and pictures thus imaged are synthesized to constitute a whole image. In order to image several times, only a detecting unit is moved and an X-ray source is substantially fixed with respect to the object. Images thus obtained include a common part of the object and are joined so that the common part are overlapped on each other. In case where an image pick-up tube is included in the detecting unit, the image pick-up tube is made operable, after a period of time necessary for attenuation of microphonic noise has lapsed, measured from a point of time where the detecting unit has been stopped.

10 Claims, 9 Drawing Sheets

X-RAY IMAGING SYSTEM AND METHOD THEREFOR

BACKGROUND OF THE INVENTION

The present invention relates to an X-ray imaging system and a method thereof. More in detail it relates to an X-ray imaging system suitable for imaging a large area such as a chest, etc. and a method thereof.

A field of view of an X-ray television imaging unit consisting of an X-ray image intensifier (herein-belong abbreviated to X-ray II) and a television camera is not sufficiently great to cover the chest described above. A usual imaging system is a so constructed that X-ray, which has been transmitted through a subject, is detected by the X-ray II. However the field of view of this X-ray II, i.e. the area, of the X-ray II input screen, is limited. By present techniques the area, of the input screen, cannot be greater than 16 inches for securing a practically usable special resolution.

In order to use an imaging system having only small field of view for imaging an object greater than the field of view, heretofore several parts of the object have been imaged separately, and images thus obtained have been joined to form a synthesized image for the whole object. Such an imaging method is disclosed in Electromedica 60 (1992) No. 1, pp. 2–5. By this method the detection unit consisting of an X-ray II and a television camera is integrated in one body with an X-ray source and both are moved simultaneously and in a same direction and stopped at a plurality of predetermined positions, where imaging is effected.

However, since X-ray emitted by an X-ray source is a substantially diverging beam, inconveniences indicated in FIG. 1 can take place.

An X-ray source 3 is integrated with an X-ray detection unit 16 in one body, which is moved parallelly to a subject 17 in a dorsal position. In this case, since an X-ray beam traversing the subject 17 is a diverging beam, when the X-ray source 3 is at A, the X-ray beam passing through a position indicated by P on a surface of the abdomen passes through a position indicated by Q on a surface of the back, while when the X-ray source 3 is at B, the X-ray beam passing through a position indicated by P on the surface of the abdomen passes through a position indicated by R on the surface of the back.

Since an X-ray image on the detection unit is formed by utilizing X-rays passed through the surface of the back, in case where two images at the positions A and B thus obtained are joined, when they are joined so that the positions indicated by P on the surface of the abdomen are overlapped on each other, on the surface of the back they are joined at Q on one of the images and R on the other. Therefore the images cannot be joined precisely.

By the prior art techniques described above, in case where imaging is effected several times by using a television camera for the X-ray detection unit while moving it, it is not possible to avoid that mechanical vibration is transmitted to the television camera. As the result, stripes which are parallel to the direction of the scanning line of the television camera (horizontal direction on the image) are generated, which gives rise to a problem that image quality is worsened. This phenomenon is called microphonic noise and explanation thereof is described e.g. in "Satsuzo Kogaku (Imaging Technology) pp. 37–40" (in Japanese) as a general phenomenon for imaging using a television camera.

SUMMARY OF THE INVENTION

The object of the present invention is to solve at least one of the problems described above.

According to an aspect of the present invention, the position of the X-ray source is substantially fixed with respect to a subject and only the X-ray detection unit is moved. According, an incident angle of the X-ray to any part of the subject is kept constant independent on the position of the detection unit. The inconvenience shown in FIG. 1 will disappear by acquiring several images each of which includes the common part (hereinafter abbreviated to a reference part) so that the images are jointed to overlap the reference part thereof.

In order to reduce exposure dose by X-ray for the subject, it is preferable to dispose means for making X-ray emitted by the X-ray source pass only in the direction towards the detection unit. In an embodiment there was disposed a slit between the X-ray source and the subject, which was so constructed that the position of the opening thereof was moved, depending on the position of the detection unit. In an embodiment, in which an X-ray tube was used for the X-ray source, the orientation of the X-ray tube was varied around a fixed axis so that it was possible to irradiate always an object with an even distribution in intensity of the X-ray.

A first image made when the detection unit is at the first position and a second image made when the detection unit is at the second position are joined to obtain a synthesized image by a well-known method. At this time it is preferable to overlap the parts corresponding to the reference part included in the different images on each other. A concrete synthesizing method is described in the U.S. patent application Ser. No. 08/186471 filed on Jan. 26, 1994, now U.S. Pat. No. 5,485,500. The content of this application is incorporated herein by reference.

The detection unit in this embodiment is so constructed that an X-ray II, a television camera and an optical system coupling them are incorporated in one body. In an embodiment this detection unit is moved parallelly to a grid's surface.

According to another aspect of the present invention, in order to prevent influences of the microphonic noise described previously, timing of imaging by means of the television camera is characteristic. That is, the television camera is put in a state where it can read-out, after a period of time necessary for attenuation of the microphonic noise has lapsed, measured from a point of time where position change of the detection unit from the first position (or second position) to the second position (or first position) has been completed. In order to prevent displacement caused by the movement of the subject, it is preferable that timing of the irradiation with X-ray is directly after the position change of the detection unit has terminated. Further, in order to keep the period of time necessary for attenuation of the microphonic noise constant, it is preferable to keep temperature of the image pick-up tube of the television camera constant.

The concept described above of preventing influences of the microphonic noise is not necessarily restricted to application to an X-ray imaging system, but it can be applied to all types of imaging systems using a television camera effecting movement of displacement.

BRIEF DESCRIPTION OF THE DRAWINGS

These and other objects and technical advantages of the present invention will be readily apparent from the following description of the preferred exemplary embodiments of the invention in conjunction with the accompanying drawings, in which.

DESCRIPTION OF THE PREFERRED EMBODIMENTS

Hereinbelow a first embodiment of the present invention will be explained in detail, referring to related figures.

Figure 2:
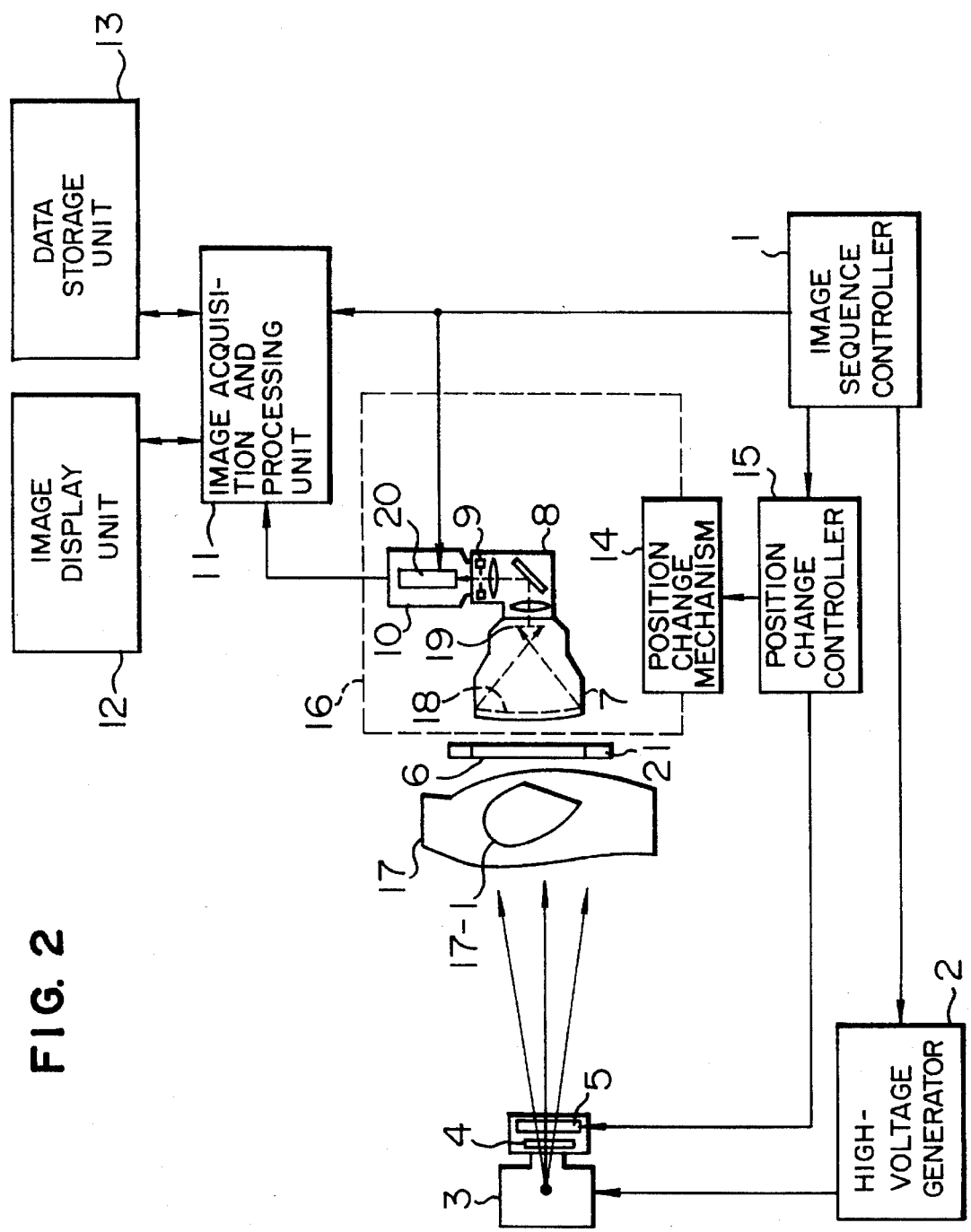
FIG. 2 is a side view showing whole construction of a digital X-ray imaging system related to an embodiment of the present invention.

FIG. 2 is a side view showing a schematical construction of a digital X-ray imaging system for chest related to the embodiment. The digital X-ray imaging system for chest related to the embodiment is composed of an imaging-sequence controller 1; a high-voltage generator for X-ray tube 2; an X-ray tube 3; an X-ray filter 4; an X-ray slit 5; an X-ray grid 6; an X-ray II 7; an optical lens and mirror unit 8; an iris 9; a television camera 10; an image acquisition and processing unit 11; an image display unit 12; a data storage unit 13; a position change mechanism 14 for moving the X-ray detection unit 16 enclosed by a broken line; a position change controller 15; etc. The position of the subject 17 is standing.

Figure 1:
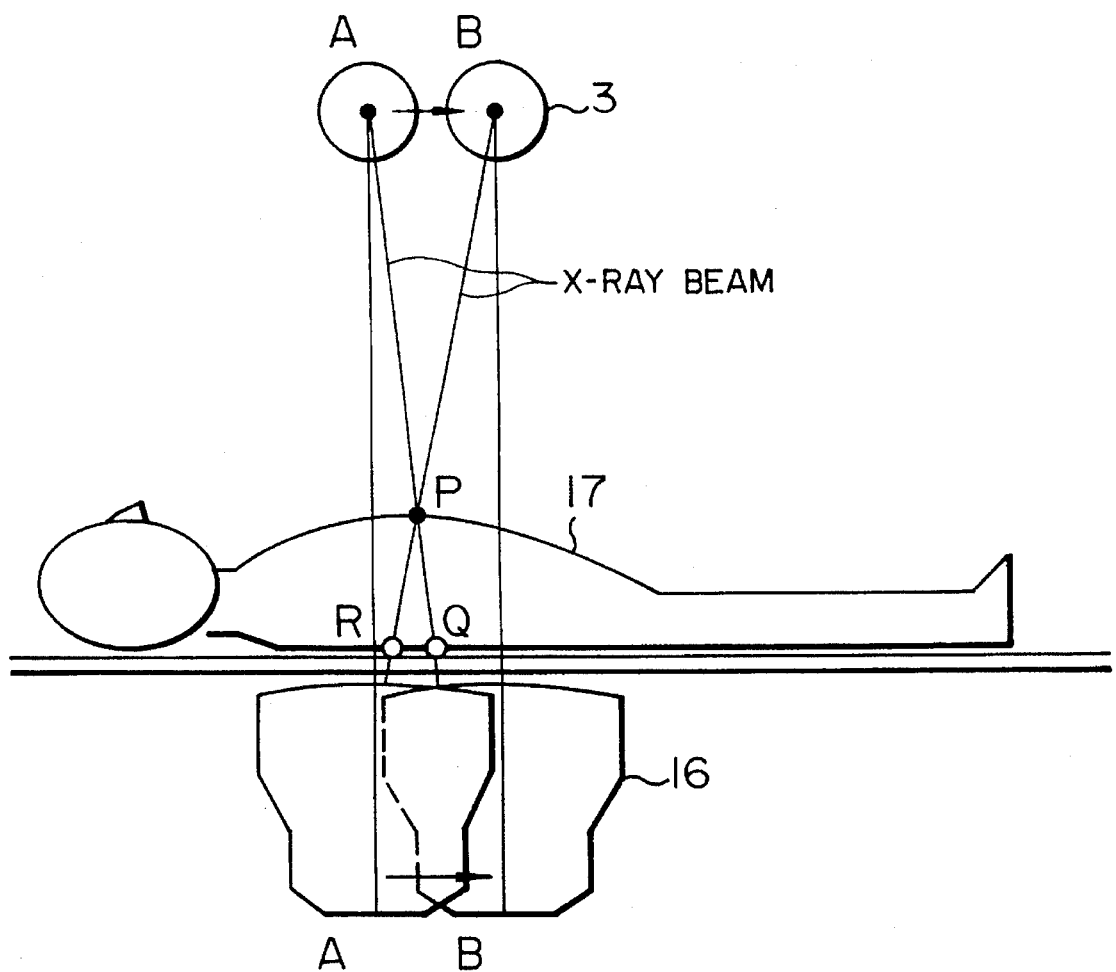
FIG. 1 is a diagram showing a prior art X-ray imaging method.
Figure 3:
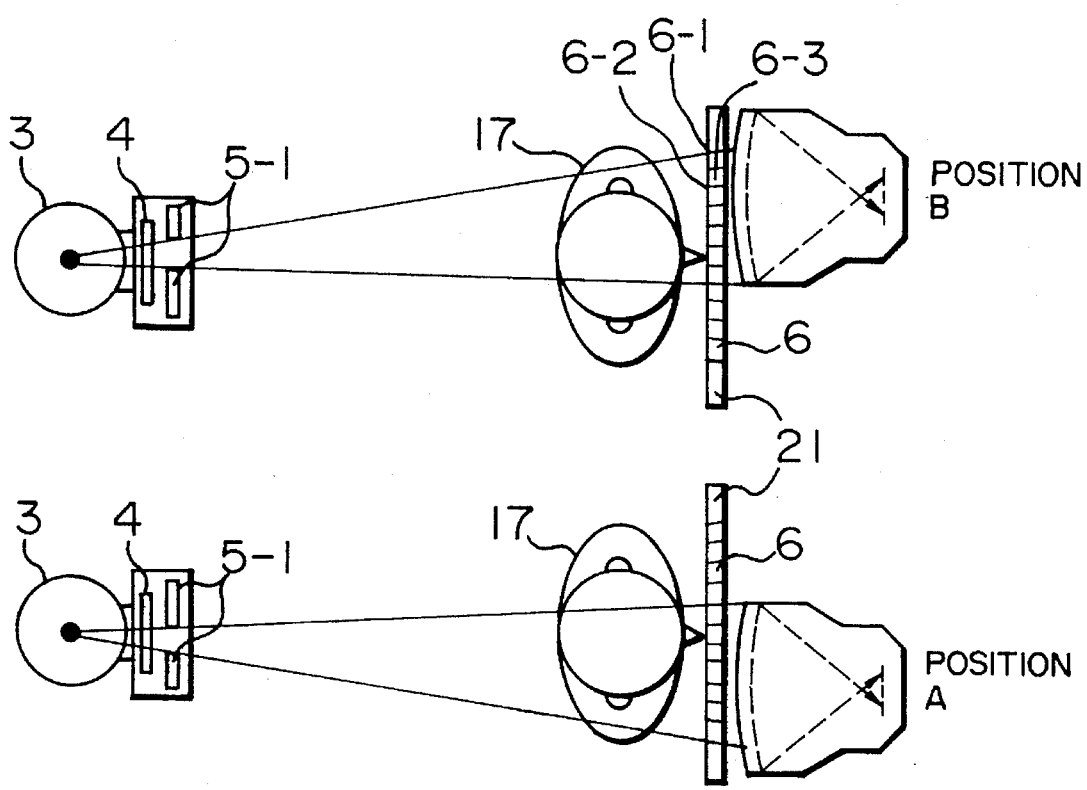
FIG. 3 is a top view of the digital X-ray imaging system indicated in FIG. 2.
Figure 5A:
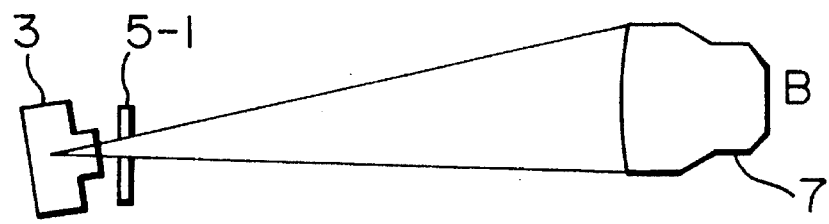
FIG. 5A and 5B are a conceptional diagram indicating variations of X-ray tube.
Figure 5B:
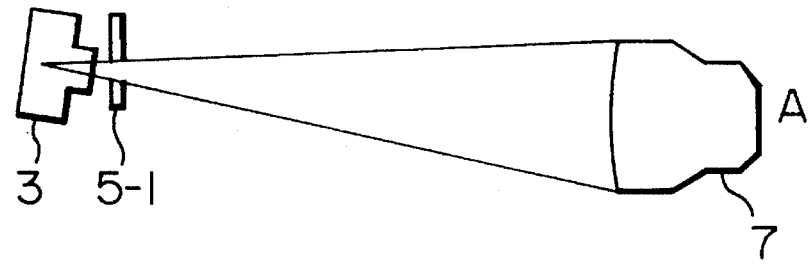

FIG. 3 is a top view showing a schematical construction of the imaging system in the X-ray imaging system described above. The present system images the chest by two exposures. A and B indicate positions of the detection unit at imaging, which correspond to a first and a second position, respectively. In FIG. 3, 5-1 indicates a part restricting the horizontal X-ray emission region in the X-ray slit. Description of a slit restricting the vertical X-ray emission region is omitted in FIG. 3. The position A is a position, at which the detection unit covers a single lung and a mediastinum, while the position B is a position, at which the detection unit covers the other single lung and the mediastinum. In the present embodiment, in the positions A and B, the center of the detection unit are shifted from the body axis by 85 mm, respectively.

Figure 4:
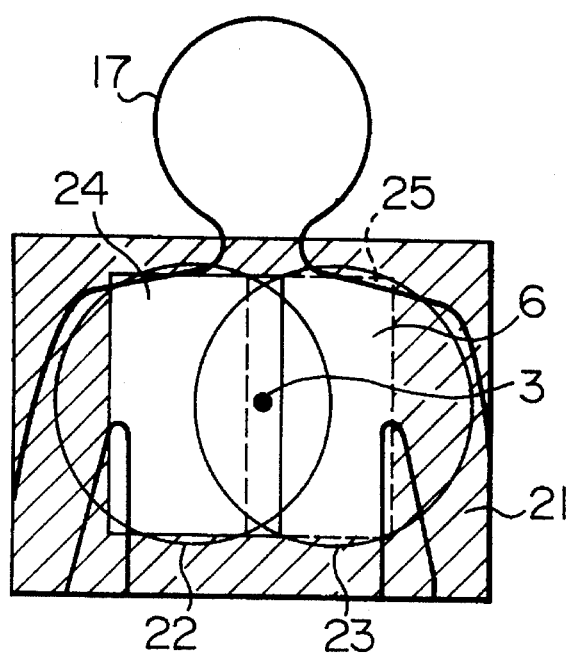
FIG. 4 is a front view showing an X-ray grid and an X-ray input screen on an X-ray detection unit in the digital X-ray imaging system indicated in FIG. 2.

FIG. 4 is a front view showing an area of the X-ray grid and the X-ray detection unit on which the X-ray is irradiated. The X-ray grid 6 is square-shaped and the circumference thereof is covered by an X-ray shielding plate 21. X-ray detection screens of the X-ray detection unit at the positions of the X-ray detection unit at the two imagings (positions A and B) described previously are indicated by circular regions 22 and 23.

The detection screen of the X-ray detection unit is an input phosphor screen 18 of the X-ray II 7, whose shape is a circle having a diameter of about 14 inches (35 cm). Relation between the detection screen of the X-ray II and an X-ray irradiation region is as follows. When the X-ray detection unit is at the position A, the X-ray irradiation region limited by the X-ray slit is indicated by 24 (enclosed by a thick line), when the X-ray irradiation region limited by the X-ray slit when the X-ray detection unit is at the position B, it indicated by 25 (enclosed by a broken line). The whole of the X-ray irradiation regions is the sum of the region 24 and the region 25, whose shape is the same square as the shape of the X-ray grid described previously. The position change direction of the X-ray irradiation region is identical to the position change direction of the X-ray detection unit, which is a horizontal direction.

The X-ray grid 6 consists of X-ray absorbing strips or narrow plates (Lead foils) (6-1, 6-2, 6-3, . . . and retainers thereof made of poor X-ray absorption such as an aluminum or the like. The X-ray grid 6 is a focusing type grid designed by supposing that the distance between the X-ray source and the X-ray grid is 2 m, whose shape is a square having sides 350 mm long. The X-ray grid 6 is disposed at a position distant from the X-ray tube 3 by 2 m so that the center line connecting the center of the grid surface with the X-ray source is perpendicular to the grid surface. The X-ray grid is so arranged that X-ray absorbing plates (6-1, 6-2, 6-3, . . ., in FIG. 3) constituting the grid 6 are perpendicular to the position change direction (horizontal direction) of the X-ray detection unit for the two imagings, i.e. in the vertical direction. The X-ray detection unit 16 is disposed so that the X-ray input phosphor screen is perpendicular to a floor surface and parallel to the X-ray grid surface.

The television camera 10 indicated in FIG. 2 is a camera having an ultra-high precision mode effecting 2100 line scanning and using a high resolution image pick-up tube for an imaging device, which is mounted so that the scanning direction thereof is parallel to the position change direction of the X-ray detection unit for the two imagings and the position change direction of the region irradiated with X-ray. Further the scanning direction is perpendicular to the X-ray absorbing plates constituting the X-ray grid 6.

The outline of the function of each of the parts described above is as follows.

The imaging-sequence controller 1 determines the imaging sequence for X-ray imaging by means of the X-ray detection unit 16 located at the two predetermined positions, i.e. positions A and B, i.e. pulse width and pulse interval of two shots of pulsely irradiated X-ray, voltage applied to the X-ray tube, tube current, working mode of the television camera, position change sequence of the opening in the X-ray slit 5-1 and position change sequence of the X-ray detection unit 16. The position change controller 15 can keep a standing state of the X-ray detection unit 16 at each of the two predetermined positions described above and move it between the two shots of X-rays while keeping parallellism thereof to the grid surface of the X-ray grid by controlling the position change mechanism 14. Further it moves the opening of the X-ray slit 5-1 in the same direction as the position change direction of the X-ray detection unit 16 by means of a position change mechanism not indicated in the figure. In this way it is possible to carry out successively the two X-ray imagings at two kinds of positions described previously.

The high-voltage generator 2 generates voltage and current according to the imaging sequence so that X-ray is pulsely produced by the X-ray tube 3. The X-ray filter 4 absorbs low energy X-ray. It is used for the purpose of reducing exposure dose and increasing contrast of the image by decreasing scattered X-rays. X-ray, which has been transmitted through the subject 17, is injected into the component thereof has been eliminated by the grid 6. The field of view of the input to the X-ray II 7 covers a region of a single lung and the mediastinum.

An X-ray image projected to the input phosphor screen 18 of the X-ray II 7 is transformed into a visible image which is enhanced in illumination on the output phosphor screen 19 owing to working an electron optics in the X-ray II 7. The optical lens and mirror unit 8 focuses this visible image on the television camera 10. The television camera 10 transforms the image into video signals, which are outputted to the image acquisition and processing unit 11.

The image acquisition and processing unit 11 A/D-converts the video signals stated above and stores them in an internal frame memory. Two digital X-ray images thus obtained are corrected in geometrical distortions in the images due to the X-ray detection unit and in shading of density level of the images. The two images are joined to obtain a synthesized image so that the parts of the subject included in the two images in common are overlapped on each other, which is subjected further to image processing. The image thus obtained is displayed on the image display unit 12 and stored in the memory unit 13. The image display unit 12 has a function of displaying both the single lung images and the synthesized image and it is possible also to observe the right and left single lung images juxtaposed right and left.

In the present embodiment an X-ray television camera consists of an X-ray II 7, a television camera 10 and an optical system coupling them. In this way, real-time detection of the X-ray and display thereof is possible and also imaging positioning is also easily made possible. Further, since it is possible to read out an image in real time, succeeding imaging is made possible in a short time, after the X-ray detection unit has been moved to an imaging position, and continuous imaging is also possible.

The method, by which an image pick-up tube is used for the imaging device, is a method, for which technical development is most advanced and most widely utilized as a real time X-ray imaging system, by which it is possible also to utilize an ultra-high precision camera, for which the number of scanning lines is 2100 or 4200, and which is characterized in that a high resolution X-ray image can be relatively easily obtained. An image pick-up tube is used as an imaging device for the television camera and mounted so that the scanning direction thereof is perpendicular to the X-ray absorbing plates constituting the X-ray grid, i.e. it is horizontal, because the X-ray detection unit is mounted so that the scanning direction thereof is parallel to the position change direction of the X-ray detection unit for a plurality of imagings.

According to the present embodiment, an effect can be obtained that joining of the two images is not influenced by distortion or non-uniformity of the X-ray detection unit but it can be realized with a high precision by joining two digital X-ray images thus obtained to get a synthesized image so that the parts of the subject included in the images in common are overlapped on each other after having subjected them to correction of sensitivity non-uniformity and geometric distortion correction.

Further another effect can be obtained that by covering the circumference of the X-ray grid with X-ray shielding plates and covering the part, which is not covered by the grid stated above, in the X-ray input phosphor screen of the X-ray detection unit with X-ray shielding plates, it is possible to prevent direct incidence of X-ray into this part and to prevent worsening of image quality by halation in the X-ray detection unit.

Owing to the fact that an image pick-up tube is used for the imaging device of the television camera and that the scanning direction is set so as to be parallel to the position change direction of the X-ray detection unit for the two imagings, positioning of the images obtained by the two imagings can be effected only by parallel translation and thus an effect can be obtained that operations for generation and processing of the synthesized image are simplified, which shortens the period of time necessary from the two imagings to the generation of the synthesized image.

Further, owing to the fact that the shape of the sum region of the X-ray irradiation regions is the same square as the X-ray grid and that the region where irradiation with X-ray is doubled by the two imagings is limited to the neighborhood of the area around joining line of the two images alone, an effect of preventing unnecessary exposure of the subject to X-ray can be obtained and at the same time another effect is obtained that generation of unnecessary scattering of X-ray within the subject is decreased, which prevent lowering of image quality due to scattered X-ray.

For a television camera using an image pick-up tube, since an ultra-high precision camera, for which the number of scanning lines is increased to 2100 or 4200, has generally a lower resolving power in the scanning direction than in the direction perpendicular thereto, in the case of the present embodiment where the X-ray absorbing plates constituting the X-ray grid are perpendicular to the scanning direction of the image pick-up tube, an effect can be obtained that the image of the X-ray absorbing plates stated above, i.e. the grid pattern, fades in the imaged picture and constitutes no obstacle in diagnosis by view with the eye.

In the imaging of a chest, owing to the fact that the X-ray grid is of focusing type and that the X-ray absorbing plates constituting the X-ray grid is parallel to the mediastinum, i.e. perpendicular to the position change direction of the X-ray detection unit for the two imagings, an effect of reducing irradiation with scattered component of the X-ray onto the detection screen for the image of the mediastinum can be obtained. Further, in the imaging of a chest, owing to the fact that the X-ray detection unit has an input field of view including the whole of a single lung and the mediastinum, an effect can be obtained that two imagings are sufficient, which is the smallest number of imagings.

Further, although the opening of the slit 5-1 is moved in the above embodiment, there is another method, by which the X-ray tube and the X-ray slit are moved, as indicated in FIG. 5, so that an axis of emitted X-ray from the X-ray tube and a center of the opening of the X-ray slit 5-1 stated above with respect to the imaging positions of the X-ray detection unit are in coincide with each other. In this way it is possible to keep X-ray intensity distribution constant, to reduce the size of the focal point and to raise the resolving power.

As another embodiment it is also possible to use a CCD device for the imaging device of the television camera and to construct it so that the arrangement of pixels thereof is parallel to the position change direction of the X-ray detection unit for a plurality of imagings. When an image pick-up tube is used, noise can be produced in an image read out directly after it is subjected to mechanical vibration under influences of vibration of constructional parts within the image pick-up tube. On the contrary, when a CCD device is used, since it is a solid device and there is no noise due to vibration, it is possible to image a picture directly after the position change of the detection unit. Further, since time difference between the plurality of imagings can be shortened, an effect can be obtained that discontinuity in the area around joining line of the image due to movement of the subject can be reduced. In the present embodiment, for various constituent devices except for the position change mechanism 14 and the position change controller 15 those used in an X-ray apparatus (Model DR2000H) supplied by Hitachi Medical Corporation can be utilized.

The present invention is not limited to the embodiments, but it can be realized, modified as indicated in the following examples.

The imaged posture of the subject is not necessarily standing, but the present invention is useful also for a subject in a dorsal position.

The field of utilization of the X-ray imaging method according to the present invention is not restricted to chest imaging, but the present invention is useful also for X-ray imaging of a large organ such as e.g. a great intestine of a big subject. Further, since the area around joining line of images can be displayed smoothly, it is suitable for diagnosis of a vascular system using a contrast medium for blood vessel.

Further, the digital X-ray imaging system according to the present invention can be used for many applications, for which a prior art X-ray imaging system can be used, and further enlarges these fields of utilization. For example, it can extend tomographic imaging, enlarging imaging, stereo imaging, etc. to imaging having a larger field of view and a higher precision than heretofore.

As explained in detail in the above, according to the first embodiment of the present invention, owing to the fact that joining of images is effected with a high precision, that direct X-ray is transmitted by a subject with a high efficiency by intercepting scattered X-ray and that the subject and the X-ray detection unit are shielded from X-ray in unnecessary fields of view, a remarkable effect can be obtained that it is possible to realize an X-ray imaging method and a system for realizing it which can image with X-ray a portion of the subject larger than the field of view of the X-ray detecting device with a high spatial resolution, while preventing unnecessary exposure.

More concretely speaking, in the DR (digital radiography) for a chest, owing to the fact that joining of images is effected with a high precision, that direct X-ray is transmitted by a subject with a high efficiency by intercepting scattered X-ray and that the subject and the X-ray detection unit are shielded from X-ray in unnecessary fields of view, an effect can be obtained that it is possible to realize an X-ray imaging system which can image with X-ray a portion of the subject larger than the field of view of the X-ray detecting device with a high spatial resolution, while preventing unnecessary exposure.

Hereinbelow a second embodiment of the present invention will be explained in detail, referring to related figures.

Figure 6:
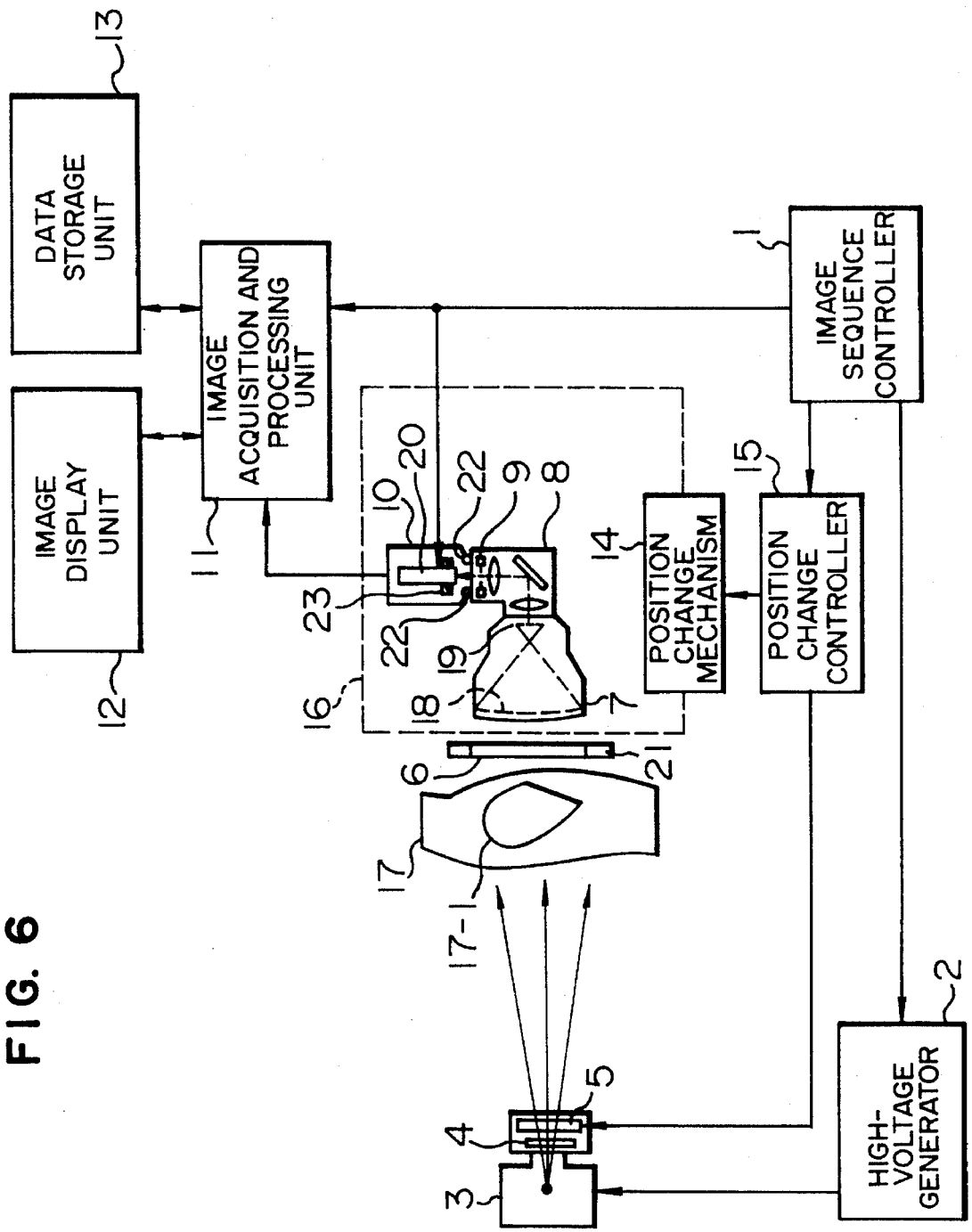
FIG. 6 is a side view showing a schematical construction of a digital X-ray imaging system for chest in a second embodiment of the present invention.

FIG. 6 is a side view showing a schematical construction of a digital X-ray system for chest in the second embodiment of the present invention. The items identical to those indicated in FIG. 2 are referred to by the same reference numerals and explanation thereof is partially omitted.

The television camera 10 used in the present invention can effect scanning with 2100 lines and 4200 lines. Although 2 biasing light sources 22 are indicated in this figure, they are in reality a plurality of light emitting diodes arranged on a circle around the iris 9. The biasing light sources 22 emit a light with even intensity with which an image detecting screen of the television camera is irradiated so that responsibility of the television camera is increased. Further a cooling device 23 consisting of a part made of metal (e.g. indium) covering the circumference of the image pick-up tube 20 and a part cooling it (part constructed e.g. by a Peltier element), in which the metal part is cooled by applying a voltage to the Peltier element. Heat produced at cooling is evacuated by air cooling.

Figure 7:
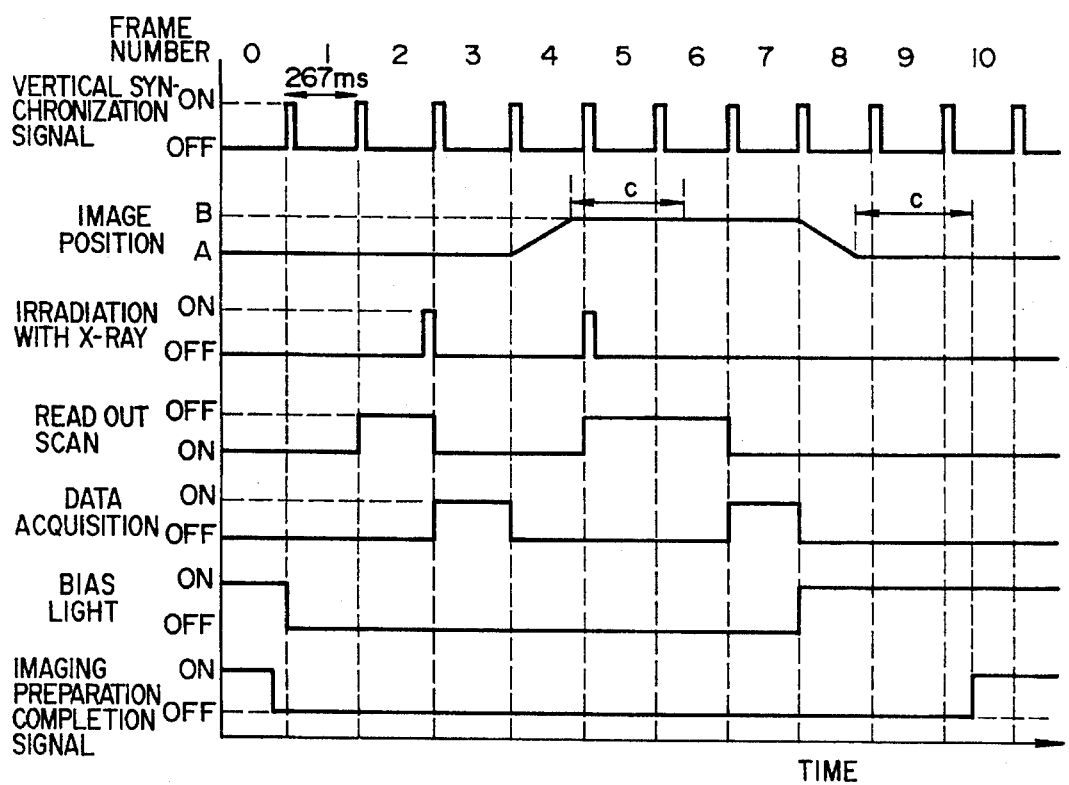
FIG. 7 is a diagram indicating an imaging sequence and a position change sequence for the digital X-ray imaging system in the second embodiment of the present invention.

FIG. 7 is a diagram indicating an imaging sequence and a position change sequence for the digital X-ray imaging system in the second embodiment of the present invention, which shows an example in case where period of time for carrying out the position change of the detection unit is effected in the time one frame of the television camera.

The working mode of the television camera is a scanning mode of 3.75 frames per second and 2100 lines and the figure shows a case where one frame time is 267 ms. The detection unit is located previously at the position A and an imaging preparation completion signal is set at ON at completion of imaging preparation. When an imaging start command is received, the imaging preparation completion signal is turned to OFF, bias light previously given from the directly succeeding frame (first frame) is reduced to zero or decreased, and an image of the bias light is subjected to idle reading.

In the ideal reading, signals for an image to be detected are read out by a scanning electron beam in the image pick-up tube, but image acquisition is not carried out and unnecessary signals for image are deleted. At the succeeding second frame, television camera's read-out scan (the scan of the electron beam in the image pick-up tube) is stopped to render the image detection plane of the television camera a state of accumulating image on it. A shot of pulsed X-ray for a first imaging is irradiated (an irradiation of X-ray) so that an image of X-ray is accumulated on the image detection plane of the television camera. At the succeeding third frame, the television camera 10 reads out the signals for image, which are accumulated on the image detection plane of the television camera as a distribution of charge by the first imaging, to output the signals to the image acquisition and processing unit to store therein. At the succeeding fourth frame the detection unit is moved to the position B. At the fifth frame after the completion of the position change, image read-out scan is again stopped and the subject is irradiated with pulsed X-ray for the second imaging to accumulate another X-ray image on the image detection plane of the television camera. A state where image read-out scan is stopped is continued during frames, for which a period of time from the point of time where the position change is terminated to the end of the frames is longer than a predetermined period of time necessary for attenuation of microphonic noise of the image pick-up tube (c in FIG. 7 indicating a case of 300 ms), i.e. during the fifth and sixth frames in FIG. 7. During the period of time, the state of accumulating the signals for the image is kept owing to the stop of scanning with the electron beam in the image pick-up tube. At the succeeding seventh frame, the television camera reads out the X-ray image according to the second imaging so that the signals for image accumulated on the image detection plane of the television camera are sent to the image acquisition and processing unit to store therein. At the succeeding eighth frame the detection unit is moved to the position A and irradiation with bias light is restarted. The imaging preparation completion signal is turned again to ON at a point of time where the predetermined period of time c necessary for attenuation of microphonic noise of the image pick-up tube has lapsed after the termination of the position change, i.e. a point of time within the tenth frame. The frame, in which the X-ray slit controlling the X-ray irradiation region is moved, is the same as the frame, in which the X-ray detection unit is moved. A representative example of the width of the pulsed X-ray is 30 ms. Since the joining of the two images cannot be effected precisely, if the subject moves between the two imagings, it is preferable that time interval between the two irradiations with X-ray is as short as possible. For this purpose it is preferable that irradiation with X-ray is effected in the neighborhood of the end of the frame for the first imaging, while irradiation with X-ray is effected in the neighborhood of the beginning of the frame for the second imaging.

Figure 8:
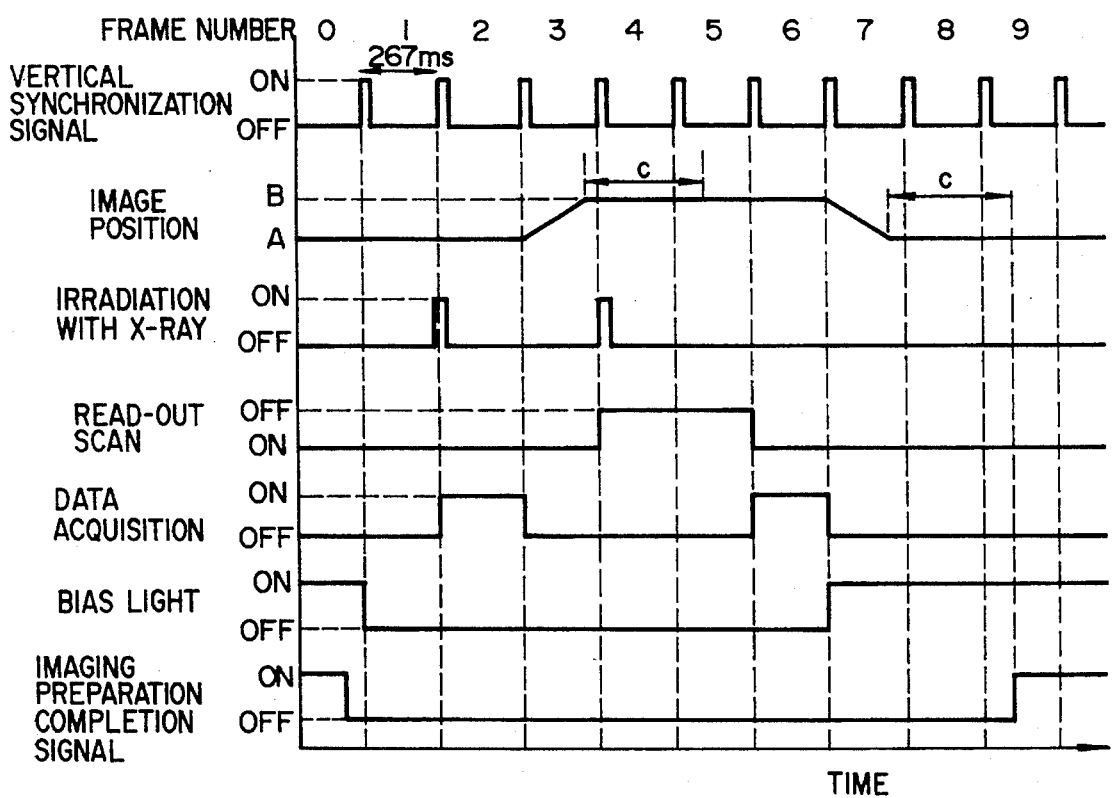
FIG. 8 is a diagram indicating an imaging sequence and a position change sequence for the digital X-ray imaging system in the third embodiment of the present invention.

FIG. 8 is a diagram indicating an imaging sequence and a position change sequence for the digital X-ray imaging system in the third embodiment of the present invention.

The present embodiment is characterized in that image read-out scan is not stopped at imaging the first picture. That is, when an imaging starting command is received, the imaging preparation completion signal is turned to OFF, bias light previously given from the directly succeeding frame (first frame) is reduced to zero or decreased, and an image of the bias light is read idly. Then the subject is irradiated with pulsed X-ray for the first imaging during a black-out period between the first frame and the second frame. At the second frame first video signals are read-out and stored in the image acquisition and processing unit as the first imaged picture data. Operations at the third and the following frames are identical to those described for the fourth and following frames of the embodiment indicated in FIG. 7.

According to the present embodiment an effect can be obtained that the period of time from the reception of the imaging start command to the real start of imaging or the termination of imaging is shortened by one frame with respect to the case indicated in FIG. 7.

Figure 9:
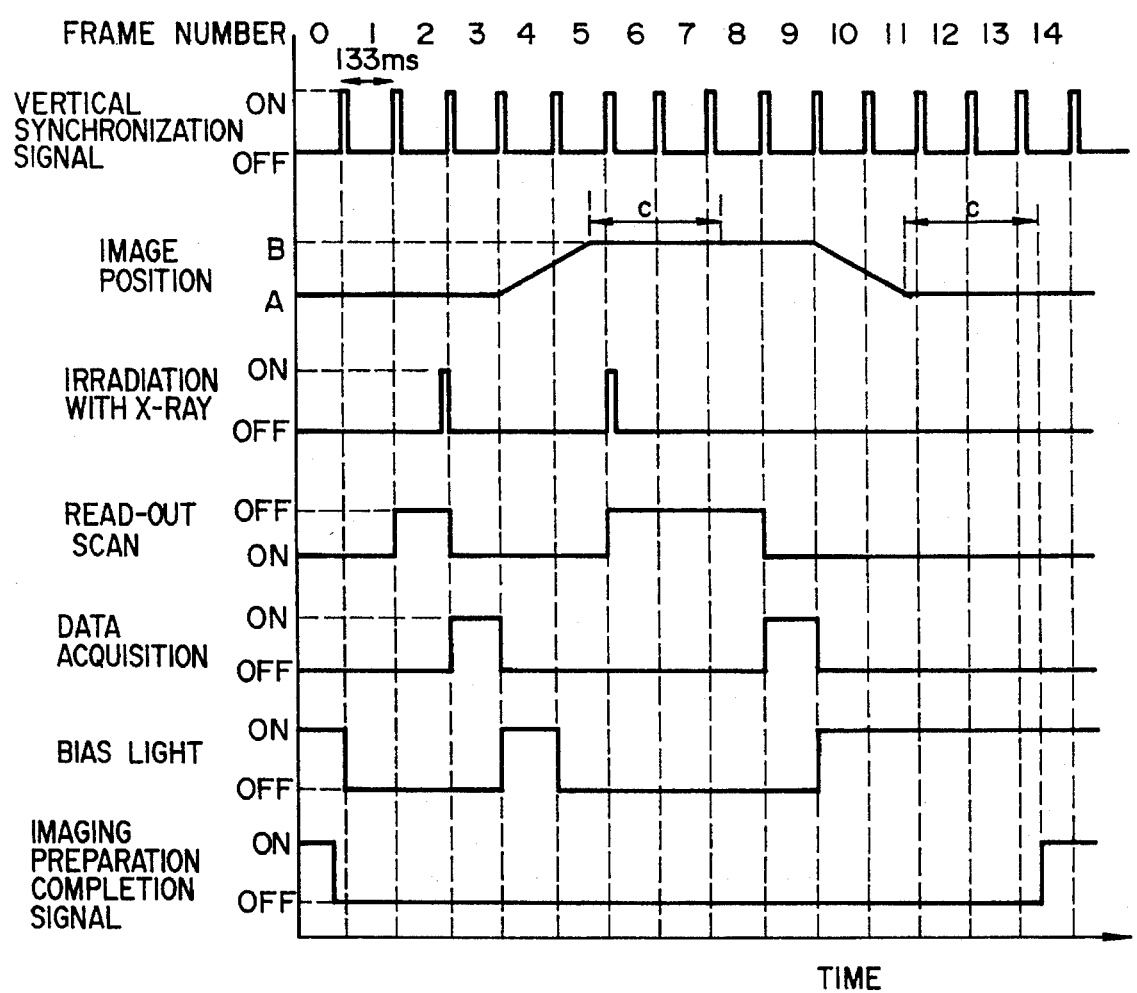
FIG. 9 is a diagram indicating an imaging sequence and a position change sequence for the digital X-ray imaging system in the fourth embodiment of the present invention.

FIG. 9 is a diagram indicating an imaging sequence and a position change sequence for the digital X-ray imaging system in the fourth embodiment of the present invention, which shows an example in case where position change of the detection unit is effected in two frames.

The working mode of the television camera is a scanning mode of 7.5 frames per second and 2100 lines and the figure shows a case where one frame time is 133 ms. The position change of the detection unit is terminated within 267 ms, i.e. within two frames, similarly to the case indicated in FIG. 7. The detection unit is located previously at the position A and an imaging preparation completion signal is set at ON at completion of imaging preparation. When an imaging start command is received, the imaging preparation completion signal is turned to OFF, bias light previously given from the directly succeeding frame (first frame) is reduced to zero or decreased, and an image of the bias light is read idly. At the succeeding second frame television camera read-out scan is stopped and then the subject is irradiated with pulsed X-ray for the first imaging. At the succeeding third frame signals for the first image are read-out and stored in the image acquisition and processing unit as the first imaged picture data. At the succeeding two frames, i.e. the fourth frame and the fifth frame, the detection unit is moved to the position B. At the sixth frame after the completion of the position change, image read-out scan is again stopped and the subject is irradiated with pulsed X-ray for the second imaging. A state where image read-out scan is stopped is continued during frames, for which a period of time from the point of time where the position change is terminated to the end of the frames is longer than a predetermined period of time c necessary for attenuation of microphonic noise of the image pick-up tube (in FIG. 9, a case of 300 ms is indicated, similarly to FIG. 7), i.e. till the eighth frame in FIG. 9. At the ninth frame the signals for second image are read-out and stored in the image acquisition and processing unit as the second image data. At the succeeding tenth and eleventh frames the detection unit is moved to the position A and irradiation with bias light is restarted. The imaging preparation completion signal is turned again to ON at a point of time where the predetermined period of time c necessary for attenuation of microphonic noise of the image pick-up tube has lapsed after the termination of the position change, i.e. a point of time within the fourteenth frame. The frame, in which the X-ray slit controlling the X-ray irradiation region is moved, is the same as the frame, in which the X-ray detection unit is moved. Also in the embodiment indicated in FIG. 9, a sequence, by which the whole imaging operation is shortened by one frame, is possible similarly to the embodiment indicated in FIG. 8 with respect to the embodiment indicated in FIG. 7.

In the embodiments indicated in FIGS. 7, 8 and 9, an effect can be obtained that the rise time of signal current in the output of the image pick-up tube at reading is shortened, because bias light is given previously thereto. Further, since bias light is reduced to zero or decreased from the frame directly preceding the frame, where the subject is irradiated with X-ray, to the data acquisition frame, another effect of increasing dynamic range of the detection unit at data acquisition can be obtained.

In the embodiments indicated in FIGS. 7, 8 and 9, an effect is obtained that a period of time till a succeeding imaging can be made as short as possible by returning the detection unit to its initial imaging position and setting an imaging preparation completion signal directly after the signals for second imaging have been read out.

Further these embodiments have following effects.

By using an image pick-up tube having a diameter of about 2 inches (5 cm) for the imaging device of the television camera it is possible to obtain images of higher resolution with respect to a case where an image pick-up tube having a diameter of ⅔ inches (1.7 cm) or 1 inch (2.5 cm) is used. Although the period of time necessary for attenuation of microphonic noise can be elongated when the diameter of the image pick-up tube increases, influences thereof can be reduced according to the present invention.

According to the embodiments 2 to 4 of the present invention, in the DR for chest, it is possible to realize an X-ray imaging system, which can image with X-ray a portion of the subject larger than the field of view of the X-ray detection unit with a high spatial resolution by reducing microphonic noise in images and by effecting joining of images with a high precision.

Further the field of utilization of the embodiments 2 to 4 is not restricted only to digital X-ray imaging, but they are useful for all sorts of imaging, for which vibration of the detection unit has influences on images.

The above embodiments concerns the X-ray imaging system, and it is not limited to the X-ray imaging system and is applicable to general imaging systems for views or the like in which visible light is used. That is, the above embodiment is applicable when a visible image is imaged at a desired stop position by a movable television camera.

Figure 10:
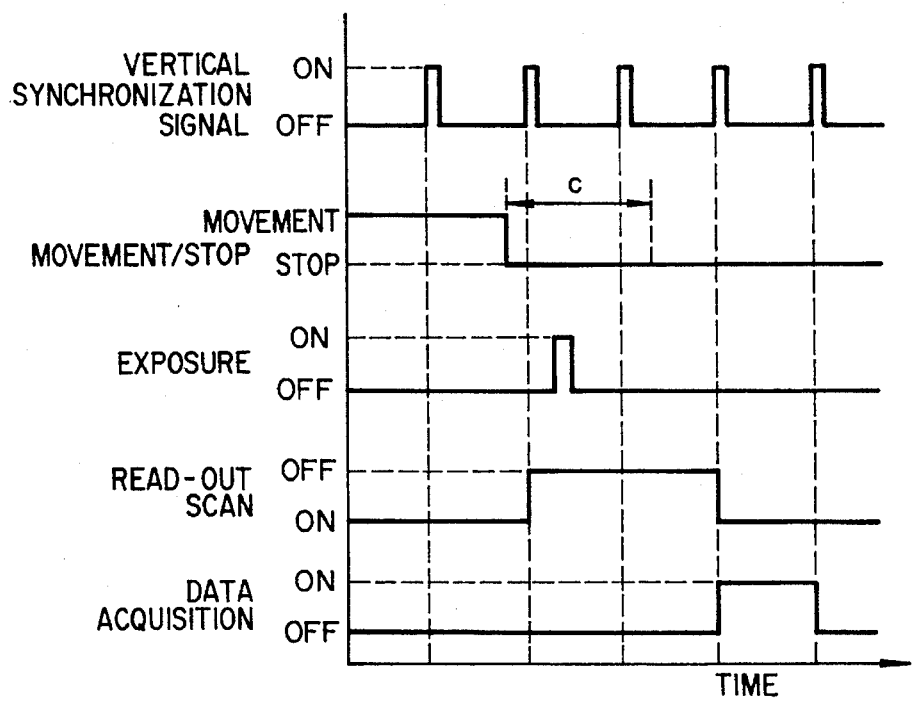
FIG. 10 is a diagram indicating an imaging sequence and a position change sequence for the digital X-ray imaging system in the fifth embodiment of the present invention.

FIG. 10 is a diagram indicating an imaging sequence and a position change sequence for a general imaging system in the fifth embodiment of the present invention.

In the present embodiment an example of strobo imaging for a visible image of a subject is shown, in which a television camera, whose imaging device is an image pick-up tube, is used and the subject is exposed by a light pulse in a still state after the image pick-up tube has been moved. The image read-out scan of the television camera is stopped at a frame, in which the subject to be imaged is irradiated with the pulsed light, after the termination of the position change of the detection unit of the television camera, and a state where image read-out scan is stopped is continued during frames, for which a period of time from the point of time where the position change is terminated to the end of the frames is longer than a predetermined period of time c necessary for attenuation of microphonic noise of the image pick-up tube. After the stop of the image read-out scan has been removed, signals for image are read out and stored in the data acquisition unit.

Figure 11:
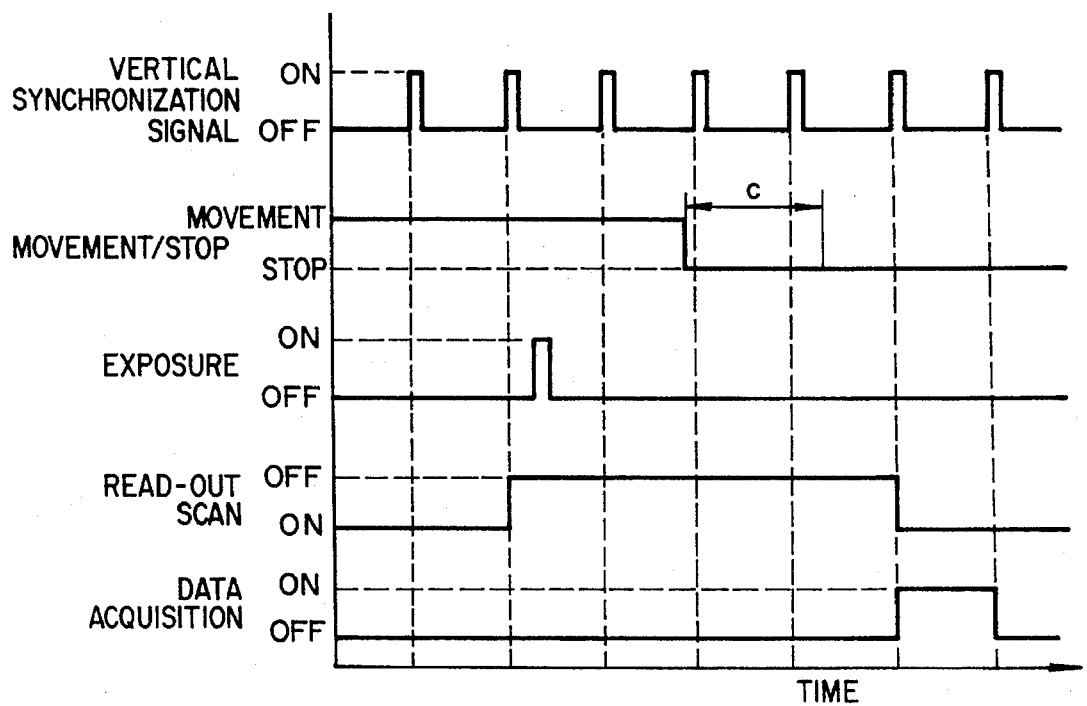
FIG. 11 is a diagram indicating an imaging sequence and a position change sequence for the digital X-ray imaging system in the sixth embodiment of the present invention.

FIG. 11 is a diagram indicating an imaging sequence and a position change sequence for imaging system in the sixth embodiment of the present invention.

In the present embodiment an example of strobo imaging is shown, in which a subject to be imaged is irradiated with a pulsed light during the television camera moves. The image read-out scan of the television camera is stopped at an exposing frame, and a state where image read-out scan is stopped is continued till a frame, which ends after a point of time where a predetermined period of time necessary for attenuation of microphonic noise of the image pick-up tube has lapsed. After the stop of the image read-out scan has been removed, signals for subject's image are read-out and stored in the data acquisition unit.

What is claimed is:

1. A picture imaging system comprising:
    a television camera having an image pick-up tube;
    means for moving and stopping said television camera;
    means for exposing an object to be imaged after said television camera has been turned-over from a moving state to a stopped state; and
    means for making said television camera read out image signals of said object to be imaged, after a period of time of at least 300 ms for attenuation of microphonic noise has lapsed, measured from a point of time where said television camera has been turned-over from the moving state to the stopped state.

2. A picture imaging system according to claim 1, further comprising means for maintaining temperature of said television camera constant.

3. A picture imaging system comprising:
    a television camera having an image pick-up tube;
    means for moving and stopping said television camera;
    means for exposing an object to be imaged while moving said television camera; and
    means for making said television camera read out image signals of said object to be imaged, after a period of time of at least 300 ms for attenuation of microphonic noise has lapsed, measured from a point of time where television camera has been turned-over from the moving state to the stopped state.

4. An imaging method by means of an imaging system including a television camera having an image pick-up tube, means for moving said television camera, and means for exposing an object to be imaged; said method comprising the steps of:
    exposing the object to be imaged after said television camera has been turned-over from a moving state to a stopped state; and
    making said television camera read out image signals, after a period of time of at least 300 ms for attenuation of microphonic noise has lapsed, measured from a point of time where said television camera has been turned-over from the moving state to the stopped state.

5. An imaging method by means of an imaging system including a television camera having an image pick-up tube, means for moving said television camera and means for exposing an object to be imaged said method, comprising the steps of:
    exposing the object to be imaged while moving said television camera; and
    making said television camera read out image signals, after a period of time of at least 300 ms for attenuation of microphonic noise has lapsed, measured from a point of time where said television camera has been turned-over from a moving state to a stopped state.

6. An X-ray imaging system comprising:
    a substantially fixed X-ray source with respect to a subject to be imaged;
    detecting means for detecting an X-ray transmitted through said subject, wherein said detecting means located at a first position detects said X-ray transmitted through a first part of said subject, and said detecting means located at a second position detects said X-ray transmitted through a second part of said subject, said first part and said second part of the subject being partially overlapped, and said detecting means includes an X-ray image intensifier, a television camera having an image pick-up tube and an optical system coupling said X-ray image intensifier and said television camera;
    a grid disposed between said subject and said detecting means;
    moving—stopping means, which moves said detecting means and stops said detecting means at said first or said second position;
    control means for controlling said television camera to read out image signals, after at least a period of time of at least 300 ms for attenuation of microphonic noise has lapsed, measured from a point of time where position change of said detecting means from either one of said first position and said second position to the other has been completed;
    processing means for processing output signals from said detecting means to form an image of said subject; and
    display means for displaying said image of said subject.

7. An X-ray imaging system comprising:
    a substantially fixed X-ray source with respect to a subject to be imaged, said X-ray source emitting an X-ray for irradiating said subject;
    detecting means for detecting said X-ray transmitted through said subject, wherein said detecting means located at a first position detects said X-ray transmitted through a first part of said subject, and said detecting means located at a second position detects said X-ray transmitted through a second part of said subject, said first part and said second part of the subject being partially overlapped, and said detecting means includes an X-ray image intensifier, a television camera having an image pick-up tube and an optical system coupling said X-ray image intensifier and said television camera;

a grid disposed between said subject and said detecting means;

moving—stopping means, which moves said detecting means and stops said detecting means at said first or said second position;

first control means for controlling said X-ray source to emit said X-ray, when said detecting means is located at said first position;

second control means for controlling said television camera to read out image signals formed by irradiation with said X-ray;

third control means for controlling said X-ray source to emit said X-ray, after position change of said detecting means from said first position to said second position has been completed;

fourth control means for controlling said television camera to read out image signals, after at least a period of time of at least 300 ms for attenuation of microphonic noise has lapsed, measured from a point of time where position change of said detecting means to said second position has been completed;

processing means for processing output signals from said detecting means to form an image of said subject; and display means for displaying said image of said subject.

8. An X-ray imaging system comprising:

a substantially fixed X-ray source with respect to a subject to be imaged, said X-ray source emitting an X-ray for irradiating said subject;

detecting means for detecting said X-ray transmitted through said subject, wherein said detecting means located at a first position detects said X-ray transmitted through a first part of said subject, and said detecting means located at a second position detects said X-ray transmitted through a second part of said subject, said first part and said second part of the subject being partially overlapped, and said detecting means includes an X-ray image intensifier, a television camera having an image pick-up tube and an optical system coupling said X-ray image intensifier and said television camera;

a grid disposed between said subject and said detecting means;

moving—stopping means, which moves said detecting means and stops said detecting means at said first or said second position;

first control means for controlling said X-ray source to emit said X-ray, when said detecting means is located at said first position;

second control means for controlling said television camera to read out image signals formed by irradiation with said X-ray;

third control means for controlling said X-ray source to emit said X-ray, after position change of said detecting means from said first position to said second position has been completed;

fourth control means for controlling said television camera to read out image signals, after at least a period of time of at least 300 ms for attenuation of microphonic noise has lapsed, measured from a point of time where position change of said detecting means to said second position has been completed;

fifth control means for controlling said irradiation with said X-ray to stand-by, after at least a period of time of 300 ms for attenuation of microphonic noise has lapsed, measured from a point of time where said detecting means has been returned from said second position to said first position;

processing means for processing output signals from said detecting means to form an image of said subject; and display means for displaying said image of said subject.

9. An X-ray imaging system comprising:

a substantially fixed X-ray source with respect to a subject to be imaged, said X-ray source emitting an X-ray for irradiating said subject;

detecting means for detecting said X-ray transmitted through said subject, wherein said detecting means located at a first position detects said X-ray transmitted through a first part of said subject, and said detecting means located at a second position detects said X-ray transmitted through a second part of said subject, said first part and said second part of the subject being partially overlapped, and said detecting means includes an X-ray image intensifier, a television camera having an image pick-up tube and an optical system coupling said X-ray image intensifier and said television camera;

a grid disposed between said subject and said detecting means;

moving—stopping means, which moves said detecting means and stops said detecting means at said first or said second position;

first control means for controlling said X-ray source to emit said X-ray, when said detecting means is located at said first position;

second control means for controlling said television camera to read out image signals formed by irradiation with said X-ray;

third control means for controlling said X-ray source to emit said X-ray, after position change of said detecting means from said first position to said second position has been completed;

fourth control means for controlling said television camera to read out image signals, after at least a period of time of 300 ms for attenuation of microphonic noise has lapsed, measured from a point of time where position change of said detecting means to said second position has been completed;

processing means for processing output signals from said detecting means to form an image of said subject; and display means for displaying said image of said subject.

10. An X-ray imaging system comprising:

a substantially fixed X-ray source with respect to a subject to be imaged;

detecting means for detecting an X-ray transmitted through said subject, wherein said detecting means located at a first position detects said X-ray transmitted through a first part of said subject, and said detecting means located at a second position detects said X-ray transmitted through a second part of said subject, said first part and said second part of the subject being partially overlapped, and said detecting means includes an X-ray image intensifier, a television camera having an image pick-up tube and an optical system coupling said X-ray image intensifier and said television camera;

a grid disposed between said subject and said detecting means;

moving—stopping means, which moves said detecting means and stops said detecting means at said first or said second position;

control means for controlling said television camera to read out image signals, after at least a period of time of 300 ms for attenuation of microphonic noise has lapsed, measured from a point of time where position change of said detecting means from either one of said first position and said second position to the other has been completed;

means for maintaining temperature of said image pick-up tube constant;

processing means for processing output signals from said detecting means to form an image of said subject; and display means for displaying the image of said subject.

* * * * *